United States Patent [19]

Daeschel et al.

[11] Patent Number: 4,666,849
[45] Date of Patent: May 19, 1987

[54] LACTIC ACID BACTERIA WHICH DO NOT DECARBOXYLATE MALIC ACID AND FERMENTATION THEREWITH

[75] Inventors: Mark A. Daeschel; Roger F. McFeeters; Henry P. Fleming; Todd R. Klaenhammer; Rosemary B. Sanozky, all of Raleigh, N.C.

[73] Assignee: The United States of America as represented by the Secretary of Agriculture, Washington, D.C.

[21] Appl. No.: 539,028

[22] Filed: Oct. 4, 1983

[51] Int. Cl.$^4$ ............... C12N 1/20; C12N 15/00; C12Q 1/04; A23B 7/10
[52] U.S. Cl. ............... 435/253; 435/172.1; 435/139; 435/34; 426/49; 426/52; 426/61
[58] Field of Search ............ 435/34, 885, 253, 172.1, 435/139; 426/49, 52, 61

[56] References Cited

U.S. PATENT DOCUMENTS 3,278,393  10/1966  Bahn et al. ..................... 435/34

OTHER PUBLICATIONS

McFeeters et al., (1982) "Malic Acid as a Source of Carbon Dioxide in Cucumber Juice Fermentations", J. of Food Sci. 47, 1862–1865.
McFeeters et al., (1982) Malic and Citric Acids in Pickling Cucumbers, J. of Food Sci. 47: 1859–1861, 1865.
Stainer et al., (1976) The Microbial World, 4th ed., pp. 678–684.
Sharp, (1981) The Prokaryotes, Chap. 131-The Genus Lactobacillus, Starr et al., (eds), pp. 1658–1666.
Levine et al., (1930) A Compilation of Culture Media, p. 175.
Chalfan, Y., I. Goldberg and R. Mateles; "Isolation and Characterization of Malo-Lactic Bacteria from Israeli Red Wines"; Journal of Food Science, vol. 42, pp. 939–943, (1977).
Buchanan, R. E. and N. E. Gibbons (eds.); Bergey's Manual of Determinative Bacteriology, 8th ed., pp. 576–593, The Williams & Wilkins Co., Baltimore, MD (1974).
Fleming, H. P. and D. M. Pharr; "Mechanism for Bloater Formation in Brined Cucumbers"; Journal of Food Science; vol. 45, pp. 1595–1600, (1980).
H. P. Fleming et al., "Bloater Formation in Brined Cucumbers Fermented by Lactobacillis plantarum"; Journal of Food Science, vol. 38, pp. 499–503, (1973).
H. P. Fleming et al., "Carbon Dioxide Production in the Fermentation of Brined Cucumbers"; Journal of Food Science, vol. 38, pp. 504–506, (1973).
Kandler et al, "Zur Frange de beeinflussung der Glucosevergarung durch L-Malat bei Leuconostoc mesenteroides", Arch. Mikrobiol., vol. 90, p. 65, (1973).
Keddie, R. M.; The Properties and Classification of Lactobacilli Isolated from Grass and Silage", Journal of Applied Bacteriology, vol. 22, pp. 403–416, (1959).
Kempler et al, "Improved Medium for Detection of Citrate-Fermenting Streptococcus lactis subsp. diacetylactis"; Applied and Environmental Microbiology, vol. 39, pp. 926–927, (1980).
Miller, J. H.; Experiments in Molecular Genetics; pp. 125–127, Cold Spring Harbor Laboratory, New York, (1972).
Rogosa et al; "A Selective Medium for the Isolation and Enumeration of Oral and Faecal Lactobacilli"; Journal of Bacteriology, vol. 62, pp. 132–133, (1951).
Schultz et al, "Das 'Malatenzyme' Lactobacillus plantarum und Leuconostoc mesenteroides"; Arch. Mikrobiol., vol. 91, pp. 183–202, (1973).

(List continued on next page)

Primary Examiner—Esther M. Kepplinger
Attorney, Agent, or Firm—M. Howard Silverstein; David G. McConnell

[57] ABSTRACT

Bloating of brine fermented cucumbers can be greatly reduced by using lactic acid bacteria which do not decarboxylate malic acid and therefore do not produce carbon dioxide during fermentation. Also, certain high acid wines can be improved by fermenting fruit with bacteria which do decarboxylate malic acid.

A method has been discovered of differentiating between species of lactic acid bacteria which do and do not decarboxylate malic acid. This method comprises growing a lactic acid bacterium in a suitable malic acid-containing nutritive growth medium under conditions suitable for growth and monitoring the pH of the medium during growth. The pH will decrease only when a lactic acid bacterium is present which does not decarboxylate malic acid. When malic acid is decarboxylated, a proton is removed from the solution in accordance with the following equation:

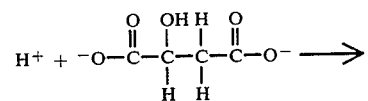

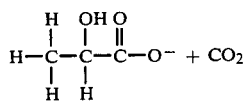

Therefore, the pH of the medium either remains the same by neutralizing lactic acid produced by the fermentation of the carbohydrate source or increases when insufficient lactic acid is present.

The above method is particularly fast and easy for screening bacteria obtained from purposely mutated species of lactic acid bacteria. Many strains of bacteria can be tested together by streaking them on a single layer agar plate.

10 Claims, No Drawings

OTHER PUBLICATIONS

Subden et al; "An L-Lactic Acid Dehydrogenase Based Method for Detecting Microbial Colonies Performing a Malo-Lactic Fermentation"; *Canadian Journal of Microbiology*, vol. 28, pp. 883–886, (1982).

Van der Westhuizen et al; "Comparison of Procedures for Isolation of Malolactic Bacteria from Wine"; *American Journal of Enol. Vitic.*, vol. 32, pp. 168–170, (1981).

Whittenbury, R.; "The Differentiation of *Streptococcus faecalis* and *S. faecium*", *Journal of General Microbiology*, vol. 38, pp. 279–287, (1965).

*The Biochemistry of Silage*, P. McDonald (ed), John Wiley and Sons, New York, N.Y., p. 131, (1981).

*Manual of Methods for General Bacteriology*, P. Gerhart (ed), American Society for Microbiology, Washington, D.C., p. 225, (1981).

Fleming et al; "Determination of Carbon Dioxide in Cucumber Brines"; *Journal of the Association of Official Analytical Chemist*; vol. 57, pp. 130–133, (1974).

LACTIC ACID BACTERIA WHICH DO NOT DECARBOXYLATE MALIC ACID AND FERMENTATION THEREWITH

BACKGROUND OF THE INVENTION

1. Field of the Invention

This invention relates to the detection and use of microbial cultures in the food processing industry.

2. Description of the Prior Art

Bloating of brine-fermented cucumbers has been attributed to the accumulation of $CO_2$ and other gases within the cucumbers [Fleming, H. P. and D. M. Pharr; "Mechanism for Bloater Formation in Brined Cucumbers"; *Journal of Food Science;* vol. 45, pp. 1595–1600; (1980)]. Fleming et al. ["Bloater Formation in Brined Cucumbers Fermented by *Lactobacillus plantarum*"; *Journal of Food Science;* vol. 38, pp. 499–503 (1973) and; "Carbon Dioxide Production in the Fermentation of Brined Cucumbers"; *Journal of Food Science;* vol. 38, pp. 504–506 (1973)] found that $CO_2$ was formed by brined cucumber tissue and by the homofermentative *Lactobacillus plantarum* during the fermentation of brined cucumbers. The combination of these two sources of $CO_2$ caused significant bloating even in controlled fermentations where other microorganisms were excluded. McFeeters et al. ["Malic acid as a Source of Carbon Dioxide in Cucumber Juice Fermentations"; *Journal of Food Science;* vol. 47, pp. 1862–1865 (1982) and; "Malic and Citric Acids in Pickling Cucumbers"; *Journal of Food Science;* vol. 47, pp. 1859–1861, 1865 (1982)] found that malate is the major organic acid in pickling cucumbers and that malate decarboxylation can account for most of the $CO_2$ produced during fermentation in cucumber juice by *L. plantarum*. Schultz and Radler ["Das 'Malatenzym' von *Lactobacillus plantarum* and *Leuconostoc mesenteroides*"; *Arch. Mikrobiol.;* vol. 91, pp. 183–202 (1973)] showed that *L. plantarum* has an active malolactic enzyme which decarboxylates malate to lactate and $CO_2$. Together, these results suggest that malate decarboxylation (MDC) is an important source of $CO_2$ in cucumber fermentations.

It would be desirable to obtain strains of lactic acid bacteria which lack the ability to produce $CO_2$ from malate, but which retain desirable characteristics for use in cucumber fermentations. However, a simple selection system is not available for rapid screening of strains or mutants of lactic acid bacteria which do (MDC+) or do not (MDC−) decarboxylate malic acid. Several methods have been used to test lactic acid bacteria for their ability to degrade malate. These entailed using tubed media with agar seals and observing $CO_2$ production from malate [Keddie, R. M.; "The Properties and Classification of Lactobacilli Isolated from Grass and Silage"; *Journal of Applied Bacteriology;* vol. 22, pp. 403–416 (1959), and; Whittenbury, R.; "The Differentiation of *Streptococcus faecalis* and *S. faecium*"; *Journal of General Microbiology;* vol. 38, pp. 279–287 (1965)], observing a rise in pH in tubed media containing malate [Whittenbury, R.; "The Differentiation of *Streptococcus faecalis* and *S. faecium*"; *Journal of General Microbiology;* vol. 38, pp. 279–287 (1965)], and assaying for the disappearance of malate and the production of lactic acid with paper chromatography [Chalfan et al.; "Isolation and Characterization of Malolactic Bacteria from Israeli Red Wines"; *Journal of Food Science;* vol. 42, pp. 939–943 (1977) and; Van de Westhuizen et al.; "Comparison of Procedures for Isolation of Malolactic Bacteria from Wine"; *American Journal of Enol. Vitic.;* vol. 32, pp. 168–170 (1981)]. None of the above methods would be practical for screening of large numbers of colonies for MDC+ or MDC− strains. Recently, Subden et al. ["An L-lactic Acid Dehydrogenase-Based Method for Detecting Microbial Colonies Performing a Malolactic Fermentation"; *Canadian Journal of Microbiology;* vol. 28, pp. 883–886 (1982)] introduced a plating medium for detecting microbial colonies performing a malolactic fermentation. The system is based upon the enzymatic detection of L-lactate, the decarboxylation product of L-malate. However, the method would only work with species that do not produce L-lactic acid from glucose, e.g., Leuconostoc. Glucose is necessary in the medium as an energy source since the malolactic reaction does not yield energy for growth [Kandler et al.; "Zur Frage de Beeinflussung der Glucosevergarung Durch L-Malat bei *Leuconostoc mesenteroides*"; *Arch. Mikrobiol.;* vol. 90, pp. 65 (1973)]. *Lactobacillus plantarum* produces DL-lactic acid from glucose [Buchanan et al. (eds.); *Bergey's Manual of Determinative Bacteriology;* 8th ed., p. 585, The Williams & Wilkins Co., Baltimore, MD (1974)], which would result in a false positive reaction on Subden's medium if the strain was MDC−.

Several other media for differential growth or selection of lactic acid bacteria have been developed. For example, LBS (Rogosa's) medium [Rogosa et al.; "A Selective Medium for the Isolation and Enumeration of Oral and Fecal Lactobacilli"; *Journal of Bacteriology;* vol. 62, pp. 132–133 (1951)] is used for the selective enumeration of lactobacilli. Kempler and McKay ["Improved Medium for Detection of Citrate-Fermenting *Streptococcus lactis* sub. sp. *diacetylactis*"; *Applied and Environmental Microbiology;* vol. 39, pp. 926–927 (1980)] developed a medium for detection of citrate-fermenting *Streptococcus lactis* sub. sp. *diacetylactis*. None of these media, however, are suitable for the differential selection of lactic acid bacteria that do not produce carbon dioxide from malic acid.

There are other areas in which a method of differentiating between MDC+ and MDC− strains of lactic acid bacteria would be useful. It is desirable to reduce acidity in certain high acid wines (Van de Westhuizen, supra). This could be accomplished by selecting only MDC+ lactic acid bacteria.

Also in the fermentation of silage for animal feed, pH should be reduced for purposes of preservation [*The Biochemistry of Silage;* P. McDonald (ed.); p. 131, John Wiley and Sons, New York (1981)]. For this, an MDC− strain of lactic acid bacteria could be selected.

SUMMARY OF THE INVENTION

We have discovered a method of differentiating between species of lactic acid bacteria which do and do not decarboxylate malic acid. This method comprises growing a lactic acid bacterium in a suitable malic acid-containing nutritive growth medium under conditions suitable for growth and monitoring the pH of the medium during growth. The pH will decrease only when a lactic acid bacterium is present which does not decarboxylate malic acid. When malic acid is decarboxylated, a proton is removed from the solution in accordance with the following equation:

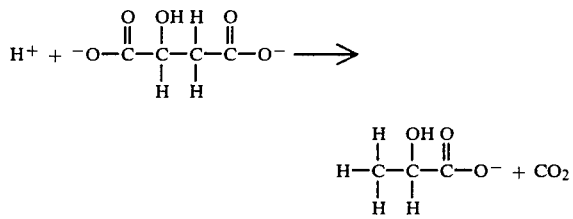

Therefore, the pH of the medium either remains the same by neutralizing lactic acid produced by the fermentation of the carbohydrate source or increases when insufficient lactic acid is present.

The above method is particularly fast and easy for screening bacteria obtained from purposely mutated species of lactic acid bacteria. Many strains of bacteria can be tested together by streaking them on a single agar plate.

DESCRIPTION OF THE PREFERRED EMBODIMENTS

The invention is generally most useful in screening large numbers of strains of lactic acid bacteria which do or do not decarboxylate malic acid and which are useful in the fermentation of malic acid-containing vegetative materials. By lactic acid bacteria, we mean those bacteria whose route of metabolism is through the glycolytic pathway. For fermentation of vegetative materials such as cucumbers and silage, the bacteria should be homofermentative (i.e., 2 moles of lactic acid is produced per mole of glucose, and an energy output of 2 ATP per mole of glucose) such as Lactobacillus and Pediococcus. Some wines require heterofermentative bacteria (i.e., 1 mole of lactic acid, 1 mole of $CO_2$, and 1 mole of acetic acid is produced per mole of glucose, and an energy output of 1 ATP per mole of glucose) such as Leuconostoc.

Suitable lactic acid bacteria include those that are naturally occurring and those that are purposely mutated. That is, naturally occurring bacteria which are treated by radiation or chemical procedures and the like which cause a heritable change in the genetic material of the organism. A preferred chemical mutagen is N-methyl-N-nitrosoguanidine. Other suitable mutagens and types of radiation are listed in *Manual of Methods for General Bacteriology* [P. Gerhart (ed.), American Society for Microbiology, Washington, DC, p. 225, (1981)].

Media suitable for growth of bacteria contain a nitrogen source, a carbohydrate source, and optionally contains essential minerals. Suitable malic acid-containing nutritive growth media (i.e., MD medium) in accordance with the invention comprise malic acid, a carbohydrate source that will yield lactic acid during fermentation with lactic acid bacteria, and amino acids or peptides as a nitrogen source. The term malic acid will be understood, herein, to include suitable salts thereof. Preferably, the carbohydrate source will be simple sugars such as glucose, fructose, sucrose, cellobiose, and the like. For optimum performance, glucose is preferred. The amino acid or peptides will preferably be those which the bacteria do not produce. A mixture of amino acids or peptides is most preferred. Suitable growth conditions and essential minerals for lactic acid bacteria are well known to those skilled in the art and will not be discussed here.

The amounts of nitrogen source in the media are those which are sufficient for the bacteria's growth requirements, and are well known to those skilled in the art. Malic acid and carbohydrate source are present in amounts within limits which are not toxic to the bacteria but are sufficient to effect a detectable change in the pH of the media. These amounts are easily determined by simple experiments. When the carbohydrate source is glucose, fructose, or the like, the ratio of malic acid to carbohydrate is preferably 1.5 to 4 parts malic acid to 1 part carbohydrate. More complex sugars may require different ratios. The medium can be used in its liquid form or a solidifying agent such as agar can be added.

Monitoring the pH of the medium can be accomplished by any suitable means known to the art. Preferably, pH is monitored by a chemical pH indicator which gives a definite color change at a pH of about 3.5 to 5.5, and which is soluble in the medium. A particularly useful indicator in this pH range is bromocresol green. In order for a chemical indicator to give a detectable color change, the initial pH of the medium is preferably in the range of about 6 to 7, most preferably about 7. If the initial pH is lower than 6, it will be too near that at which the indicator changes. If the pH is higher than 7, the reduction of the medium pH will not be enough to affect a change in color. When liquid media are used, a pH meter will effectively monitor pH. A meter could also be used in agar culture if the probes were sufficiently sensitive. When using a pH meter, a pH change could easily be detected even if the initial pH of the medium was 4.5 or less. The time required to accomplish the objective of the selection method is simply that amount of time necessary for a pH decrease to occur. This is easily determined by experiment. The use of $MDC^+$ or $MDC^-$ lactic acid bacteria is in the fermentation of malic acid-containing vegetative materials. Malic acid-containing vegetative materials include cucumbers, peppers, cabbage, tomatoes, green beans, onions, okra, olives, grapes, silage, and the like. In some of these fermentations, such as cucumbers, it is desirable to eliminate $CO_2$ formation. In others such as silage, there is a need to reduce pH. In wines, the desire is to increase pH so a $MDC^+$ bacterium is needed.

Methods of fermenting malic acid-containing vegetative materials are those which are well known in the art with the exception that the cover brines and vegetative materials should be treated to suppress and preferably eliminate all microorganisms present in the cover brine or vegetative materials which would interfere with the growth of the $MDC^-$ bacteria, thereby achieving a pure culture fermentation. The treatment can consist of sterilization of the cover brine and vegetative materials before inoculation, the addition of selective chemical suppressants, or other methods known to the art. The $MDC^-$ bacteria are added directly to the fermentation cover brine.

One embodiment of the invention is the selection of a homofermentative lactic acid bacterium which does not produce $CO_2$ (i.e., a $MDC^-$ strain), and its use in the fermentation of cucumbers. Since the malic acid in the cucumber fermentation will not be decarboxylated, the $CO_2$ formed in the fermentation medium will be limited to that formed by cucumber respiration. This will essentially eliminate the formation of bloaters (hollow pickles). In order to select an $MDC^-$ strain of bacteria to accomplish this, the preferred concentrations of glucose, malic acid, and pH indicator are as follows: (1)

glucose, 1.0–0.5% w/v, preferably 0.5 w/v; (2) L-malic acid, 1.5–2.0% w/v, preferably 2.0% w/v; (3) bromocresol green, 0.05–0.075% w/v, preferably 0.066% w/v. Suitable pH reactions of media are 6.0–7.0 preferably 7.0. the pH reaction is adjusted with suitable alkali, preferably potassium hydroxide. Bacterial cells are introduced into the liquid medium at a concentration preferably above $1 \times 10^4$ cells per ml, but generally not more than $1 \times 10^6$ cells per ml. In using the medium with a solidifying agent, the cells should be introduceed into the medium in such a manner as not to give more than 50 cells per medium container (petri plate). The inoculated medium should be incubated at a temperature suitable for growth of the bacterium under study, preferably 30° C. for the L. plantarum bacteria cited in this study. If the test is done in a liquid medium with a pure strain of bacteria, a change in color of the medium from dark blue to yellow-green indicates that the bacterium did not produce $CO_2$ from malic acid. If the liquid medium remains dark blue, the bacterium did produce $CO_2$ from malic acid. If the test is done in a solid medium with a mixture of bacterial strains, a change in color of the solid medium immediately surrounding an individual colony from dark blue to yellow-green signifies that the bacterial strain that formed the colony did not produce $CO_2$ from the malic acid. If the solid medium immediately surrounding the colony remains dark blue, the bacterium did produce $CO_2$ from malic acid. In the above manner, therefore, one may distinguish very quickly and accurately and isolate lactic bacteria that do or do not produce $CO_2$ from malic acid.

EXAMPLE 1

Liquid MD medium was used for differentiating the ability of pure strains of lactic acid bacteria to produce $CO_2$ from malic acid. An MDC$^-$ strain, L. plantarum 965, and an MDC$^+$ strain, L. plantarum WSO, were introduced into separate test tubes containing 10 ml of liquid MD medium (Table 1) without agar. Initial concentrations of bacterial cells introduced were adjusted to give concentrations of approximately $1 \times 10^6$ cells per milliliter of medium. The tubes containing medium and cells were incubated at 30° C. for 48 hr and then examined for evidence of bacterial growth and medium color change. The medium in both tubes was turbid, indicating that the bacteria in each tube had grown. The color of the liquid medium in the tube containing L. plantarum 965 had changed from dark blue to light green, indicating that this bacterium did not produce $CO_2$ from malic acid. The color of the medium in the tube containing L. plantarum WSO remained dark blue, indicating that this bacterium did produce $CO_2$ from malic acid.

EXAMPLE 2

Solid MD medium was used for differentiating the ability of pure strains of lactic acid bacteria to produce $CO_2$ from malic acid. Cell suspensions containing 50 or fewer cells (contained in 1 ml of 0.85% NaCl) of the MDC$^-$ strain, L. plantarum 965 and the L. plantarum WSO (MDC$^+$) parent strain were introduced into about 25 ml of MD medium containing solidifying agar (Table 1). The medium was poured into petri plates, which were then gently swirled to assure distribution of cells in the medium, and allowed to solidify. The pour plates were incubated at 30° C. for 4 days and examined. Colonies of bacteria were observed in petri plates containing each of the above bacteria. The color, of the solid medium immediately surrounding individual colonies of L. plantarum 965 had changed from dark blue to yellow-green, indicating that this bacterium did not produce $CO_2$ from malic acid. The color of the solid medium immediately surrounding individual colonies of L. plantarum WSO remained dark blue, indicating that this bacterium did produce $CO_2$ from malic acid.

In another test, the surface of uninoculated, solid MD medium contained in petri plates was streaked with a cell suspension of either L. plantarum 965 or WSO. The plates were incubated at 30° C. for 4 days and examined. The color of the medium immediately surrounding the resulting streak of growth indicated the ability of the bacterium to produce $CO_2$ from malic acid as given above.

TABLE 1

Formulation and preparation of "MD medium" for the detection of strains and mutants of lactic acid bacteria which do and do not decarboxylate malic acid[a]

| Component | Manufacturer | Amount/liter |
|---|---|---|
| L-malic acid | Sigma | 20 g |
| Trypticase | BBL | 10 g |
| D(+)glucose | Sigma | 5 g |
| Casamino acids | Difco | 3 g |
| Phytone | BBL | 1.5 g |
| Yeast extract | Difco | 1 g |
| Tween 80 | Atlas | 1 g |
| Bromocresol green | Fisher | 20 ml[b] |
| Agar (when desired) | Difco | 20 g |

[a]Adjust pH to 7.0 with 10N KOH. Autoclave at 15 lb pressure for 15 min. Can be stored at room temperature.
[b]Stock solution (solubilize 0.1 g in 30 ml of 0.01N NaOH).

EXAMPLE 3

Solid MD medium was used for differentiating the ability of cells of L. plantarum WSO (MDC$^+$) exposed to a chemical mutagen to produce $CO_2$ from malic acid, for the purpose of obtaining MDC$^-$ strains. Lactobacillus plantarum WSO cells were mutagenized with N-methyl-N-nitrosoguanidine (NG) according to the general procedure of Miller [Experiments in Molecular Genetics, pp. 125–137, Cold Spring Harbor Laboratory, New York, (1972)], which involved the following steps: (1) L. plantarum WSO (MDC$^+$) cells were grown for 4 hr in MRS broth (Difco), at which time they were in the logarithmic phase of growth. The cells were then diluted with sterile saline (0.85% NaCl) to about $1 \times 10^9$ cells/ml. (2) The cells were harvested by centrifugation and resuspended in citrate buffer as in Miller. (3) The cells were then mutagenized by addition of 500 μg/ml of NG to the suspended cells and holding for 90 min at 30° C. This exposure consistently gave 90% kill. (4) The cells were then washed by centrifugation and resuspended in phosphate buffer as in Miller.

After the above steps adapted from the general procedure of Miller, the following specific steps were taken in relation to the present invention: (5) The cells were centrifuged and resuspended in MRS broth and held for 3 hr at 30° C. to allow for mutant expression before pour plating with MD medium. (6) Cell suspensions containing 50 or fewer viable cells were introduced into about 25 ml of MD medium containing solidifying agar to obtain pour plates as in Example 2. (7) The plates were incubated at 30° C. for 4 days as in Example 2. (8) A total of 150 colonies was observed on a total of 10 pour plates. Four colonies, of the 150 total, were observed to be immediately surrounded by yellow-green colored medium, indicating that these bacteria did not produce $CO_2$ from malic acid (MDC$^-$); and, therefore, were mutants of the parent MDC+ strain. The remaining 146 colonies were surrounded by dark blue colored medium, indicating that these bacteria produced $CO_2$ from malic acid, and in this property, were similar to the parent strain. (9) The presumptive MDC− colonies were picked and tested for $CO_2$ production and for pH in MD media. The results of these tests for two WSO mutants (M34 and M35), the MDC+ parent culture (WSO), and the MDC−965 are given in Table 2. All strains and mutants metabolized all the glucose in the medium. The cultures giving acid reactions did not produce a significant amount of $CO_2$, hence indicating a loss in ability to produce $CO_2$ from malic acid. The parent L. plantarum WSO strain, which did not give a color change, produced a large amount of $CO_2$. The production of $CO_2$ was determined by the method of Fleming et al. ["Determination of Carbon Dioxide in Cucumber Brines"; Journal of the Association of Official Analytical Chemists; vol. 57, pp. 130-133, (1974)].

Lactobacillus plantarum WSO, the parent strain of mutant strains M34 and M35, has been taxonomically evaluated and has all the characteristics of L. plantarum species known to those skilled in the art. Strains M34 and M35 are apparently identical and presumed to possess the characteristics of the parent strain with the exception that strains M34 and M35 have lost the ability to decarboxylate malic acid. Mutant strain M35 has been deposited with the Agricultural Research Culture Collection (NRRL), Peoria, Ill., and was given the accession no. NRRL B-15422.

TABLE 2 pH reaction, $CO_2$ produced and reducing sugar concentration in MD broth fermented by strains and mutants of L. plantarum at 30° C. for 7 days

| Strains | pH | $CO_2$ mg/100 ml | % w/v Reducing sugar | Broth color |
|---|---|---|---|---|
| 965[a] | 5.19 | 16.9 | <0.02 | Light green |
| WSO[b] | 6.82 | 596.6 | <0.02 | Dark blue |
| WSO-M34[c] | 5.28 | 25.3 | <0.02 | Light green |
| WSO-M35[c] | 5.23 | 18.9 | <0.02 | Light green |
| Uninoculated control | 6.96 | 15.5 | 0.48 | Dark blue |

[a]Obtained from the National Institute for Research in Dairying, Reading, England.
[b]Obtained from USDA-ARS Food Fermentation Laboratory culture collection.
[c]Mutants of WSO.

EXAMPLE 4

Seven strains of lactic acid bacteria representing various genera and species were tested for their ability to grow in "MD medium" and produce a differentiating reaction in the medium based upon their known abilities to produce carbon dioxide from malic acid. The results are tabulated in Table 3. The Pediococcus bacteria are homofermentative strains useful in fermenting vegetative materials. Leuconostoc bacteria are heterofermentative and are used in making wine. Leuconostoc oenos PSU-1 does decarboxylate the malic acid in wine and is useful for increasing pH during fermentation.

TABLE 3

Reaction of lactic acid bacteria in MD medium after incubation at 30° C. for 1 week

| Bacterial strain | pH reaction | Color | Ability to decarboxylate malic acid |
|---|---|---|---|
| Pediococcus cerevisiae 61 | 8.58 | Blue | + |
| Pediococcus cerevisiae 39 | 8.48 | Blue | + |
| Leuconostoc paramesenteroides | 8.34 | Blue | + |
| Leuconostoc mesenteroides 43 | 5.53 | Green | − |

TABLE 3-continued

Reaction of lactic acid bacteria in MD medium after incubation at 30° C. for 1 week

| Bacterial strain | pH reaction | Color | Ability to decarboxylate malic acid |
|---|---|---|---|
| Leuconostoc mesenteroides LC-33 | 5.54 | Green | − |
| Leuconostoc dextranicum | 5.52 | Green | − |
| Leuconostoc oenos PSU-1 | 6.82 | Blue | + |

EXAMPLE 5

Lactobacillus plantarum strains WSO, M35 and 965 used in Example 3 were tested for their ability to produce $CO_2$ from naturally occurring malic acid in cucumber juice and from malic acid added to cucumber juice. The results are given in Table 4. It was observed that the M35 strain produced considerably less $CO_2$ from cucumber juice containing naturally occurring malic acid than did the parent culture WSO, indicating its MDC− character. When additional malic acid was added to sterile cucumber juice, which was subsequently fermented by strains mentioned above, there was not an increase in $CO_2$ production by the M35 strain, once again indicating its MDC− character, but there was a large increase in $CO_2$ produced by the MDC+ parent strain, WSO.

TABLE 4

$CO_2$ produced in filter-sterilized cucumber juices fermented by strains and mutants of L. plantarum at 30° C. for 7 days

| | $CO_2$ mg/100 ml | |
|---|---|---|
| Strains | Cucumber juice[a] | Cucumber juice with added malic acid[b] |
| 965 | 22.96 | 22.85 |
| WSO | 98.91 | 294.5 |
| WSO-M35 | 35.23 | 33.58 |
| Uninoculated control | 19.85 | 6.31 |

[a]Contains 20 mM malic acid.
[b]Additional malic acid added to give a 70 mM concentration.

We claim:

1. A biologically pure MDC− lactic acid bacteria which does not decarboxylate malic acid during fermentation which was produced by purposely mutating a MDC+ lactic acid bacteria which does decarboxylate malic acid during fermentation.

2. A MDC− lactic acid bacteria as defined by claim 1 produced by purposely mutating said MDC+ lactic acid bacteria with radiation.

3. A MDC− lactic acid bacteria as defined in claim 1 produced by purposely mutating said MDC+ with a chemical mutagen.

4. A MDC− lactic acid bacteria as defined by claim 3 produced by purposely mutating said MDC+ lactic acid bacteria with N-methyl-N-nitrosoguanidine.

5. A MDC− lactic acid bacteria as defined by claim 4 having the designation NRRL B-15422.

6. A method of fermenting malic acid-containing vegetative material comprising:
 a. introducing a biologically pure MDC− lactic acid bacteria which does not decarboxylate malic acid during fermentation into a cover brine containing malic acid-containing vegetative material, and
 b. fermenting said vegetative material under conditions suitable for growth of said bacteria.

7. A method of fermenting malic acid-containing vegetative material as defined by claim 6 wherein said cover brine and said vegetative material have been treated to suppress microorganisms present which would interfere with the growth of said biologically pure MDC$^-$ lactic acid bacteria, thereby achieving an essentially pure culture fermentation.

8. A method as defined by claim 6 wherein said MDC$^-$ bacteria was produced by purposely mutating an MDC$^+$ lactic acid bacteria which does decarboxylate malic acid during fermentation.

9. A method as defined by claim 8 wherein said MDC$^+$ lactic acid bacteria was purposely mutated by a chemical mutagen.

10. A method as defined by claim 9 wherein the MDC$^-$ lactic acid bacteria is designated as NRRL B-15422.

* * * * *